United States Patent [19]

Rapkin et al.

[11] Patent Number: 4,678,757
[45] Date of Patent: Jul. 7, 1987

[54] DEVICE AND METHOD FOR WHOLE BLOOD SEPARATION AND ANALYSIS

[75] Inventors: Myron C. Rapkin, Cupertino; Ronald J. Schoengold; David R. Shockey, both of San Jose; Pierre C. Van Rysselberghe, Palo Alto, all of Calif.

[73] Assignee: SmithKline Diagnostics, Inc., Sunnyvale, Calif.

[21] Appl. No.: 722,231

[22] Filed: Apr. 11, 1985

[51] Int. Cl.[4] ................... G01N 1/18; G01N 21/77; G01N 31/22

[52] U.S. Cl. ........................ 436/169; 436/170; 436/177; 436/178; 422/56; 422/57; 422/58; 422/101; 435/13; 435/805

[58] Field of Search ............... 436/169, 170, 177, 178; 422/56–58, 101; 435/13, 805

[56] References Cited

U.S. PATENT DOCUMENTS

| | | | |
|---|---|---|---|
| 3,146,163 | 8/1964 | Brewer | 422/101 X |
| 3,552,925 | 1/1971 | Fetter | 436/95 X |
| 3,552,928 | 1/1971 | Fetter | 436/169 X |
| 4,248,829 | 2/1981 | Kitajima et al. | 422/57 X |
| 4,256,693 | 3/1981 | Kondo et al. | 422/56 |
| 4,288,228 | 9/1981 | Oberhardt | 422/56 X |
| 4,330,299 | 5/1982 | Cerami | 436/95 |
| 4,476,222 | 10/1984 | Ohtani et al. | 422/56 X |
| 4,477,575 | 10/1984 | Vogel et al. | 422/57 X |
| 4,524,133 | 6/1985 | Tyhach | 435/805 X |
| 4,543,338 | 9/1985 | Chea | 436/170 |

Primary Examiner—Barry S. Richman
Assistant Examiner—Lynn M. Kummert
Attorney, Agent, or Firm—Joseph A. Marlino; Stuart R. Suter; Alan D. Lourie

[57] ABSTRACT

A method and device for separating blood into fluid and cellular fractions for diagnostic tests. The whole blood is introduced to a carrier containing a layer of carbohydrate which results in the rapid separation of the fluid from the cellular fractions. In a preferred embodiment, the device is fabricated in a sandwich design containing layers of carbohydrate and reagent material between two layers of plastic.

6 Claims, 20 Drawing Figures

U.S. Patent   Jul. 7, 1987   Sheet 1 of 6   4,678,757
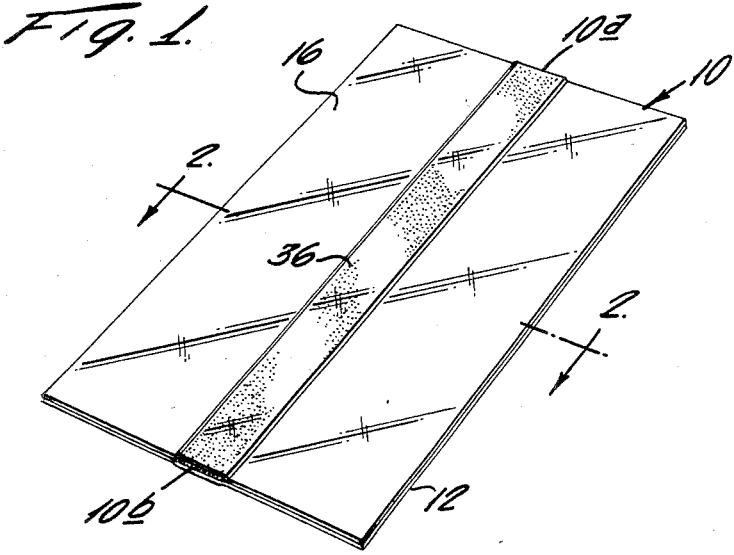
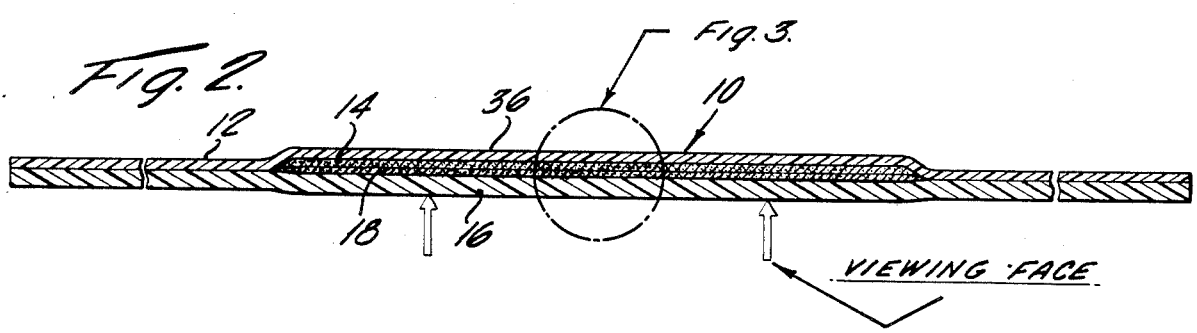
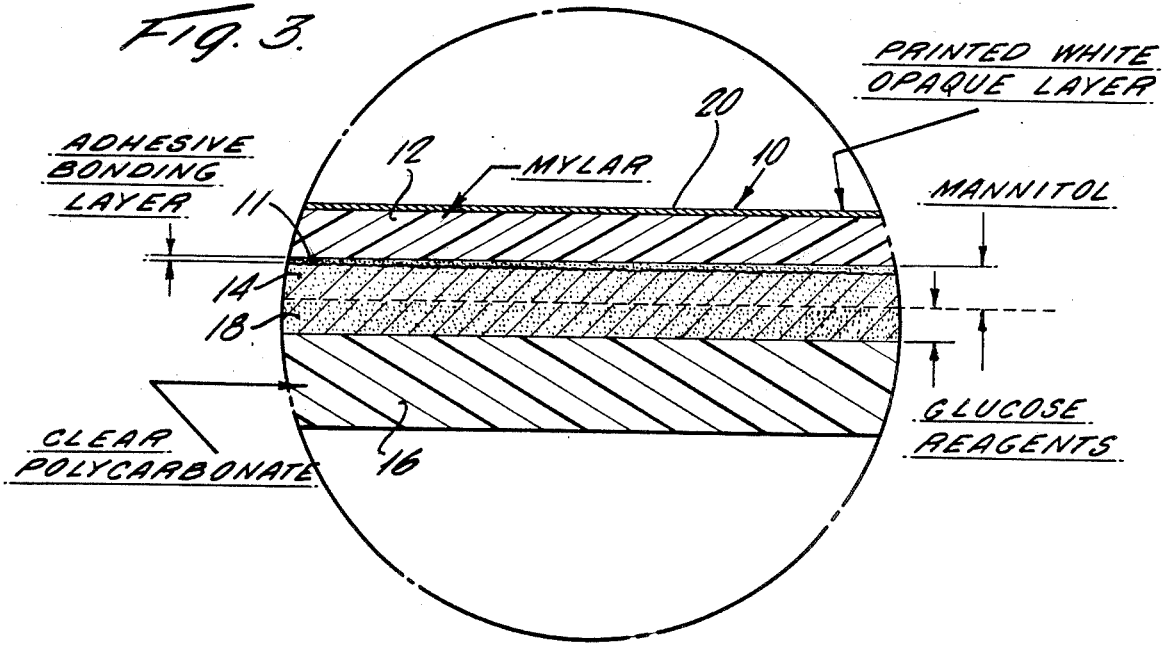

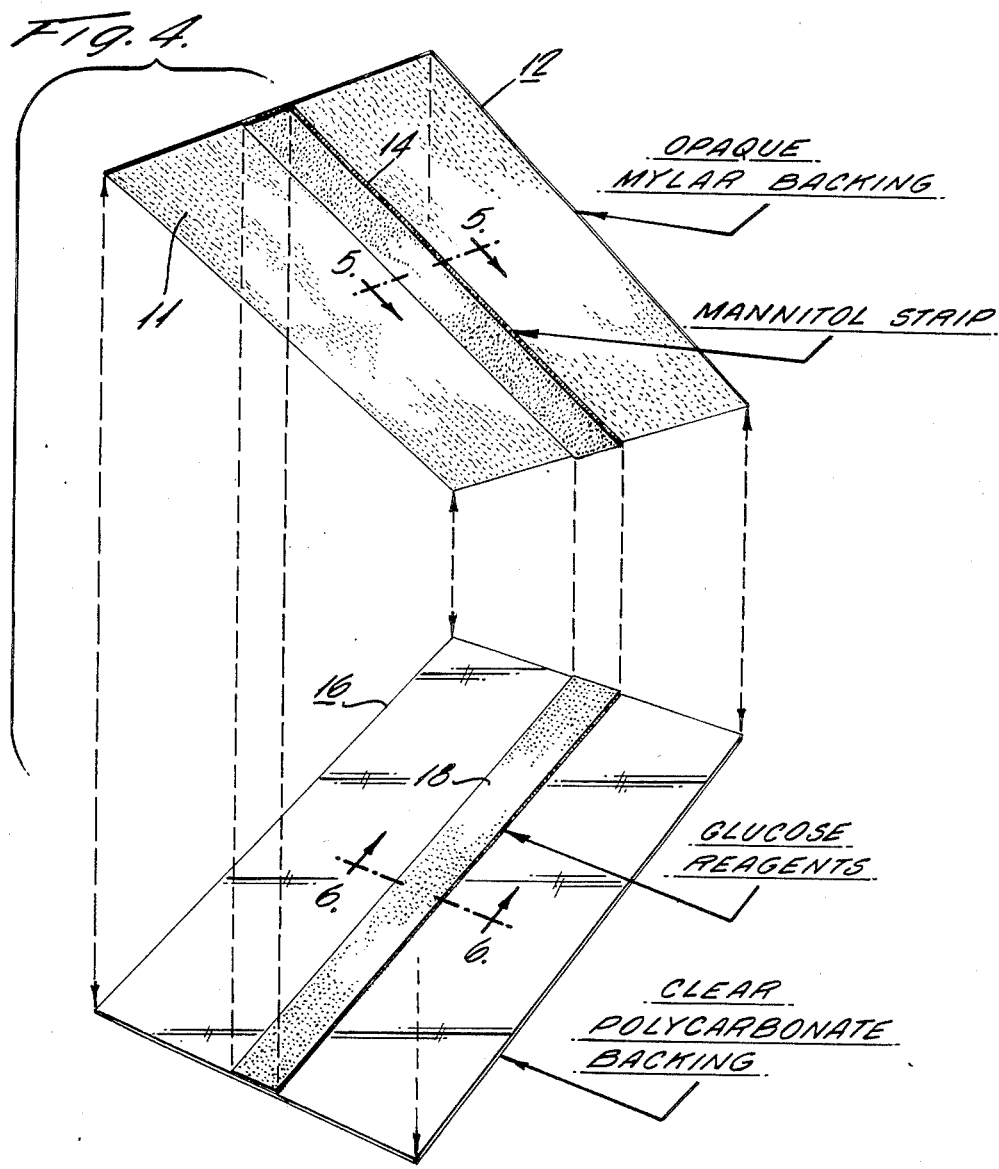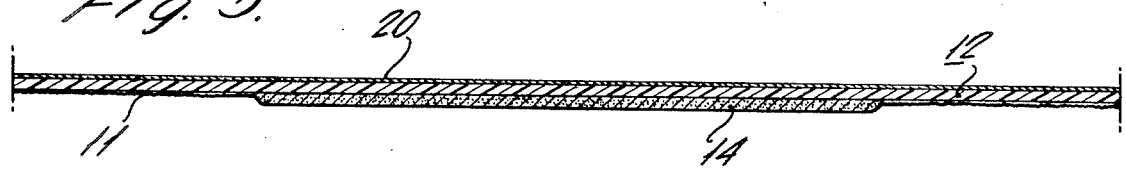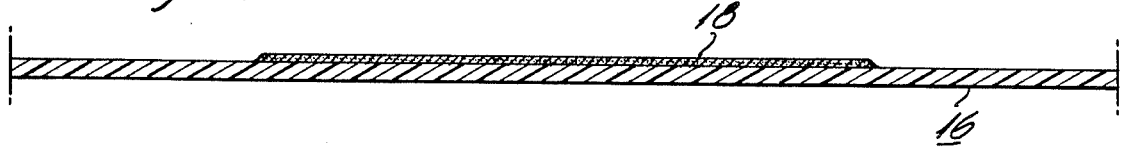

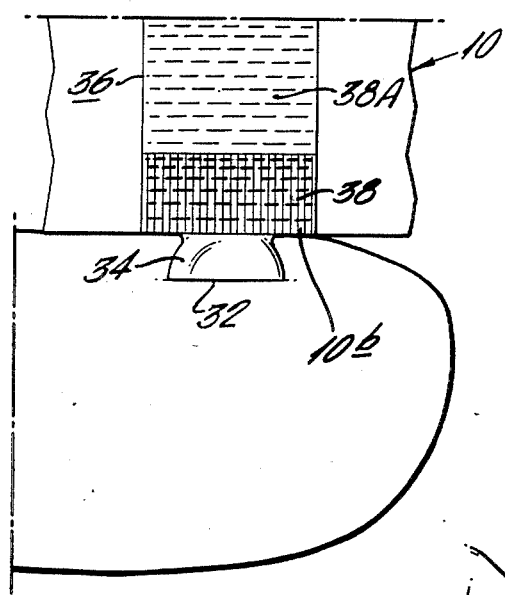
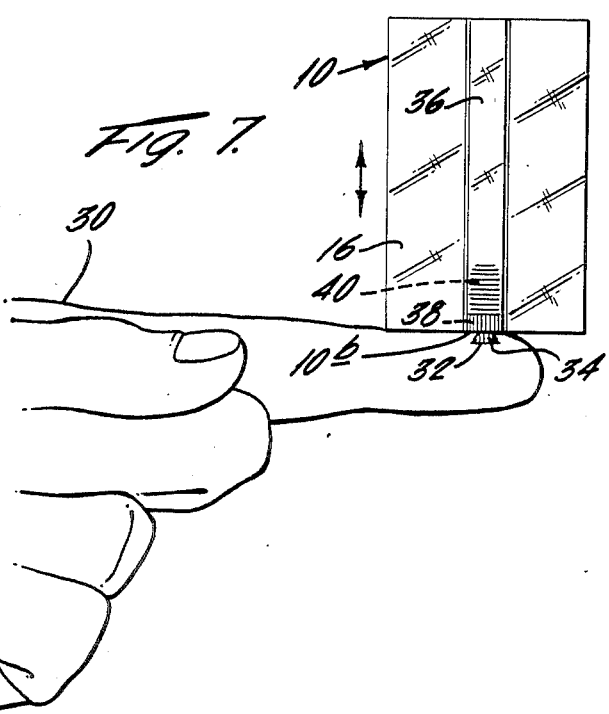
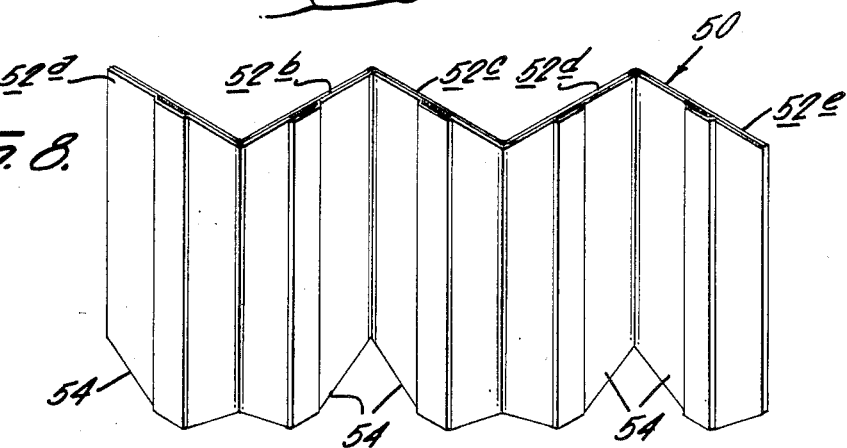
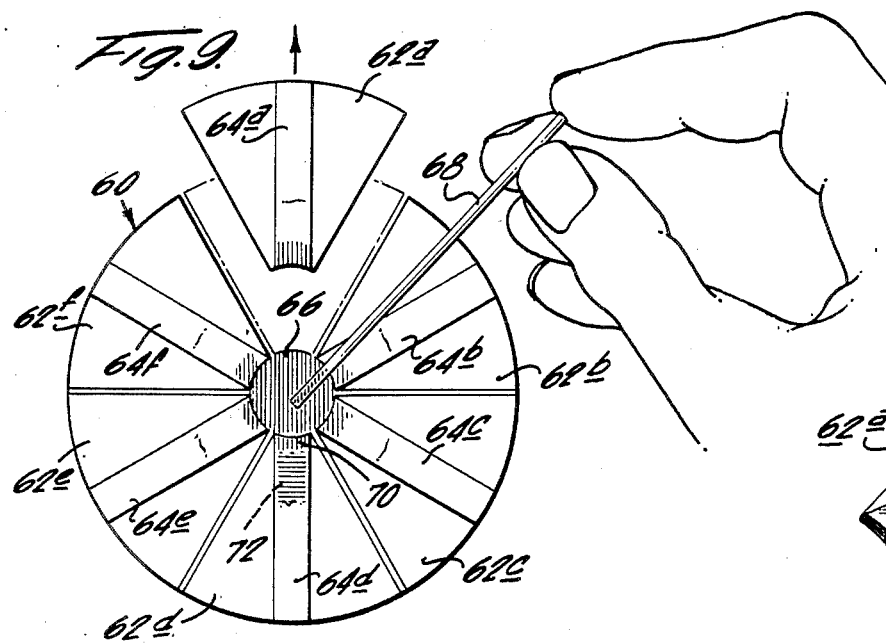

DEVICE AND METHOD FOR WHOLE BLOOD SEPARATION AND ANALYSIS

The detection of various soluble constituents in whole blood has been found to be particularly difficult. These tests usually are dependent on the visual and instrumental measurement of chromogen color formation to detect the soluble constituents. The red color of the hemoglobin therefore seriously interferes with the analysis and observations for a positive response. These tests can be simplified by prior separation of the red blood cells from the sample of whole blood. Indeed, diagnostic tests frequently require this separation.

One of the conventional methods of separating the cellular fractions from the fluid of whole blood is by centrifuging. This method of separation is very time consuming, complicated and requires extra manipulative steps and expensive laboratory apparatus. The blood is placed in a container and spun until the cellular fractions are forced to the bottom of the container and the fluid which is to be tested remains at the top. The next step is to separate the fluid from the cells by removal with a pipette. The fluid is then placed in a second container for subsequent analysis.

Great care must be taken when pipetting the fluid from the separated blood cells because there is a zone where the cells and the fluid are intermixed. Careful attention and effort is therefore necessary to ensure that the fluid is substantially cell free.

Prior methods of separating cellular fractions from fluid in whole blood have been described in U.S. Pat. Nos. 3,552,925, 3,552,928, and 3,146,163. These patents disclose the use of certain soluble and insoluble materials to effect a separation of the cellular components and the fluid.

It is therefore an object of this invention to provide a simple one step method for whole blood separation and analysis. It is a further object to provide a novel method and device for efficiently separating the whole blood into fluid and cellular fractions to facilitate subsequent diagnostic testing.

The novel method and device of this invention provides a rapid one-step process for the simultaneous separation of the fluid from the whole blood and testing for the desired component. The method provides for IN SITU separation which is much more simple, less expensive and more rapid than prior methods.

Briefly, this invention consists of a testing or sampling device which comprises a carbohydrate applied to a permeable or impermeable carrier. A permeable carrier is impregnated, printed or coated with a solution of carbohydrate and subsequently dried. The carrier may be further treated with specific reagents or diagnostic compositions which result in a chemical reaction with the fluid component.

A second and preferable embodiment includes a testing device comprising impermeable carriers. On a portion of one carrier a column of carbohydrate powder is coated and the second carrier is coated with reagents which are specific to detect a desired blood component. The separate carriers are then laminated so that the carbohydrate and reagents are in contiguous relationship. An opening in the laminated device is provided whereby the blood can directly contact the carbohydrate porous material.

The method comprises applying blood to the surface of the carbohydrate treated carrier. The fluid portion migrates away from the point of contact while the cellular components remain in close proximity to the point of contact.

If the carrier is further treated with a specific reagent employed to detect the component tested for, a color will appear in the fluid portion. An exogenous analysis can be carried out by removing a portion of the carrier containing the clear fluid with a punch and then adding the reagent.

In the method of the second embodiment the whole blood is contacted with the carbohydrate column which preferentially absorbs the colorless blood component free of cells. The cellular fraction remains at the bottom of the column and the clear fluid proceeds above the cellular fraction and comes in contact with the reagent employed to detect a specific blood component. The reaction between the component being tested for and the test reagent are then observed.

These methods thus provide a simultaneous means for separating cellular and fluid fractions of the whole blood and analyzing the fluid portion.

Exemplary of impermeable carriers which may be employed in this invention are any plastic sheet materials such as polyesters, polycarbonates, polystyrenes, polyvinyl polymers, polypropylene, polyethylene, polyethylene terephthalate (mylar), ethylcellulose and cellophane. Other impermeable carriers such as glass or wax paper may be used. Most advantageously, the side in which the results are observed will be of a transparent material and the opposite panel will be of an opaque material in order to provide a reflective background.

Exemplary of permeable carriers which may be used in this invention are filter paper, felts, fleeces, and other absorbent materials.

Preferable carbohydrates which can be employed are sugars such as:

| | |
|---|---|
| Mannitol | L(+)Arabinose |
| Sorbitol | D(+)Galactose |
| Inositol | L(−)Xylose |
| β-D Glucose | D-Glucoheptose |
| α-D-Glucose | L-Lyxose |
| D(+)Xylose | Lactose |
| D(+)Mannose | Maltose |
| D(−)Arabinose | Sucrose |

Most advantageously mannitol is the sugar employed in the device of this invention.

In regard to the reagents, the device would contain the reagent specific for the detection of the blood component being sought. For example, if testing for glucose in the blood, tetramethylbenzidine, glucose oxidase and peroxidase which are well known reagents for detecting glucose would be used in the device.

The following soluble blood components are some examples of those which may be tested for in the method according to this invention:

| | |
|---|---|
| Total Protein | Urea Nitrogen |
| Albumin | Creatinine |
| Globulin | Uric Acid |
| Bilirubin | Calcium |
| SGPT (Serum Glutamic Pyruvate Transaminase) | Cholesterol |
| | Triglycerides |
| Alkaline Phosphatase | Glucose |
| Gamma Glutamyl Transpeptidase | Theophylline |
| β-hCG (human Chorionic Gonadotropin) | Potassium |

An additional advantage of the present invention is that the soluble blood components are not affected by the carbohydrate filtration. At least ninety percent of the component found in the conventionally prepared serum is found in the fluid filtered by the separation process of this invention.

A detailed description and better understanding of this invention can be had by referring to the accompanying drawings which show a preferred embodiment of the present invention.

FIG. 1 is a perspective view of the preferred embodiment of the testing device.

FIG. 2 is an enlarged sectional view taken on line 2—2 of FIG. 1.

FIG. 3 is a greatly enlarged fragmentary sectional view of the details contained within the dot and dash circle of FIG. 2.

FIG. 4 is an exploded perspective view illustrating the various sections of construction prior to lamination.

FIG. 5 is a fragmentary view taken on line 5—5 of FIG. 4.

FIG. 6 is a fragmentary view taken on line 6—6 of FIG. 4.

FIG. 7 is a side elevational view illustrating a manner of use of the preferred embodiment of this invention.

FIG. 7A is an enlarged fragmentary schematic view illustrating the separation of fluid from the blood cells and also indicative of a negative test.

FIG. 8 is a perspective view of a modification of the preferred embodiment.

FIG. 9 is an additional preferred embodiment of FIGS. 1 through 8 of the testing device.

FIG. 10 is a perspective view of one segment of FIG. 9.

Figure 11:
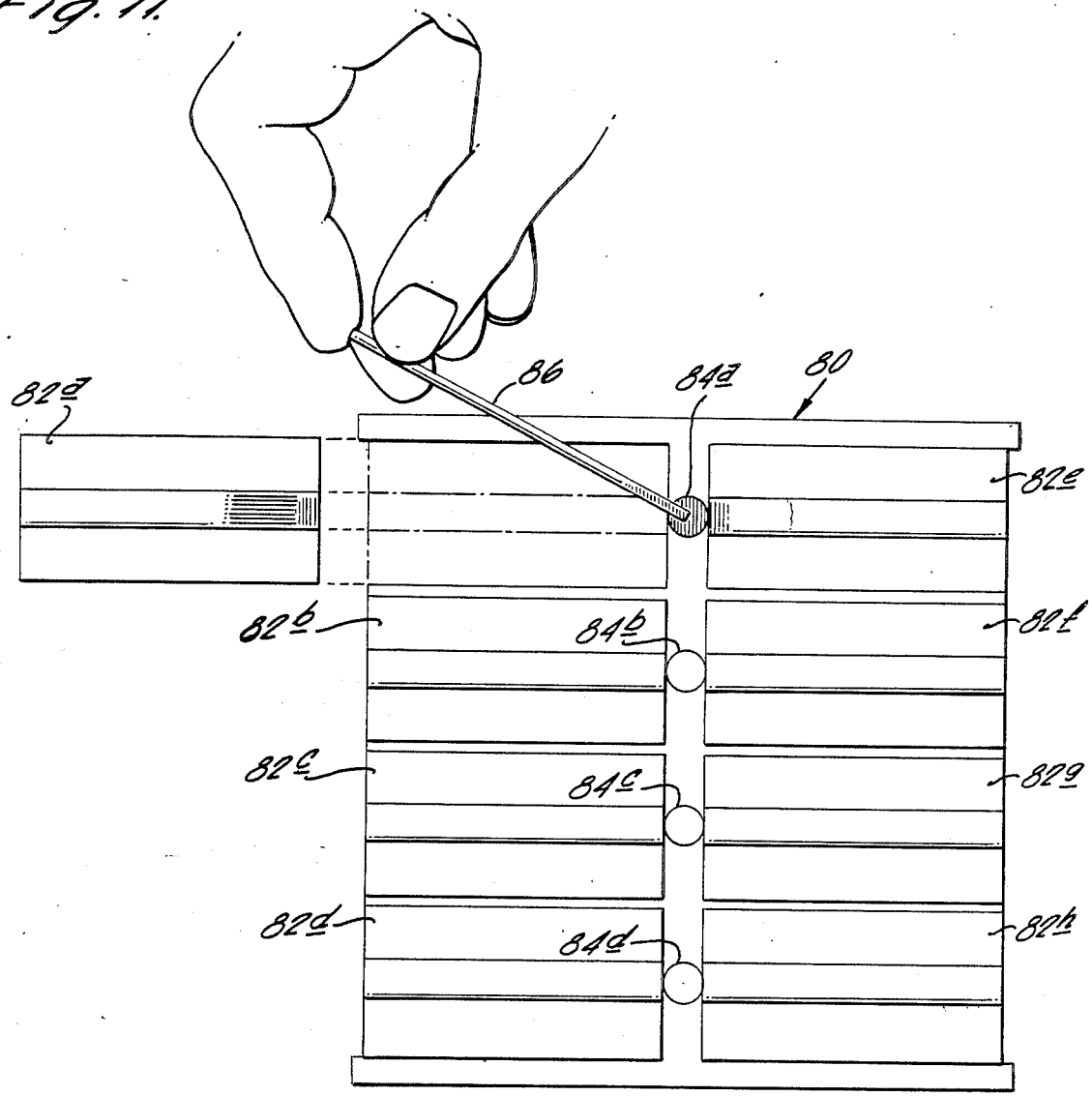
FIG. 11 is still another embodiment of the device of this invention.
Figure 12:
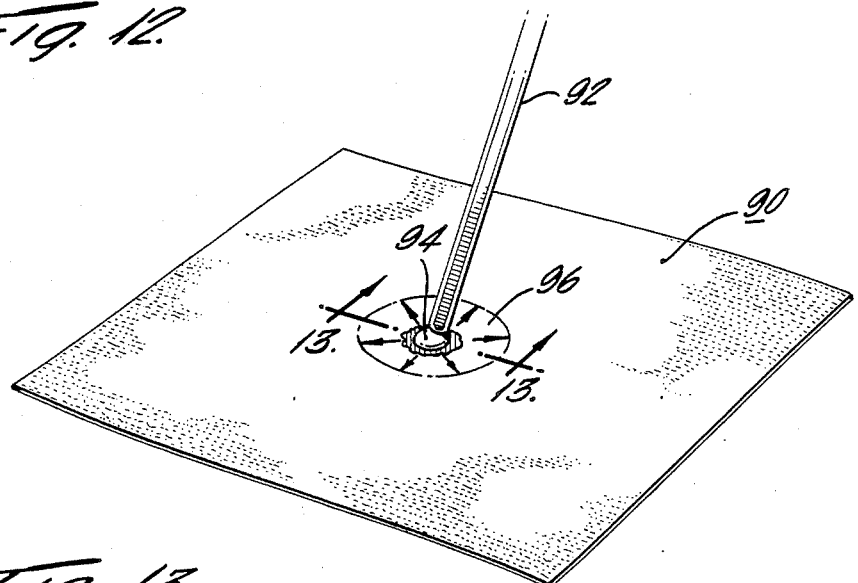
FIG. 12 is a perspective view of a further embodiment illustrating the separation of the fluid portion from the cellular portion on a permeable carrier containing a carbohydrate and indicative of a negative test.
Figure 13:
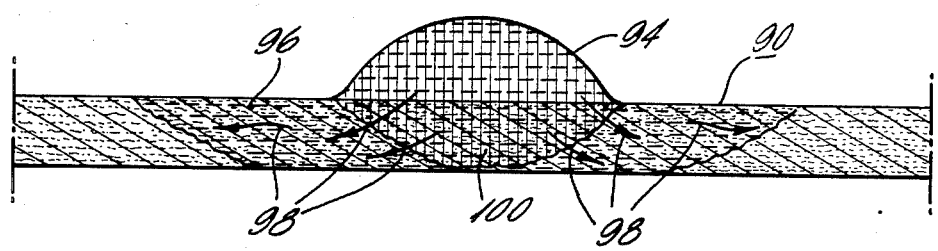
FIG. 13 is a greatly enlarged fragmentary sectional elevational view taken on the line 13—13 of FIG. 12.

As illustrated in FIGS. 1 through 3, a device 10 for separating blood into fluid and cellular fractions in accordance with the invention has an impermeable carrier 12, such as mylar, having an opaque coating 20 and a clear backing sheet 16 such as polycarbonate laminated to the opaque carrier. The mylar carrier has an adhesive precoat 11. The device has openings 10a and 10b which permit contact of the whole blood with testing area 36 which is composed of a band of dry porous material 14 such as a carbohydrate applied to the inner face of the opaque material. The backing sheet has a reagent material 18 specific to detect a desired blood component applied to its inner face. As noted in FIG. 3 the reagent and porous material 14 are in contiguous relationship after lamination.

FIG. 4 discloses the structure of the device prior to lamination, i.e., the opaque carrier with a column of dry porous material and the clear backing sheet with the desired reagent.

One method of use of the preferred embodiment is illustrated in FIGS. 7 and 7A. A puncture on the first finger 32 of the left hand 30 produces whole blood droplet 34. The testing device 10 is placed over the puncture in such a manner that the blood droplet contacts the testing area 36, which contains the column of dry porous material, through opening 10b. The blood travels by capillary action up the testing area and the porous material preferentially absorbs the fluid component of the blood 38A leaving the red cellular fractions 38 behind. In testing for a soluble blood component such as glucose, the specific reagent will stain the fluid portion as indicated at 40 if the test is positive. FIG. 7A which illustrates the separation of fluid 38A from the red cellular fractions 38 is also indicative of a negative test.

FIGS. 8 through 19 demonstrate further embodiments of the testing device of this invention. Modification 50 represents a series of devices strung together showing a plurality of panels $52^a$–$52^e$ with lower terminal ends 54 tapering to the edges of the centrally located testing area.

FIG. 9 illustrates a circular configuration of the devices shown in FIGS. 1–8 wherein multiple tests can be run. Blood can be applied to central portion 66 with a pipette 68 and the separation of the red cellular portion 70 from the fluid 72 can take place in any of the testing areas $64^a$–$64^f$ present in wedge shaped sections $62^a$–$62^f$. In this illustration the fluid 72 is stained blue to show a positive test. Each of these wedge shaped sections may also contain different reagents in the testing areas for testing various blood components.

FIG. 11 represents a rectangular shaped testing device 80 which also permits multiple testing. Blood can be applied to central portions $84^a$–$84^d$ by pipette 86 and the separation and testing results can be observed in areas $82^a$–$82^h$ which also may contain different reagents for testing separate blood components.

Figure 14:
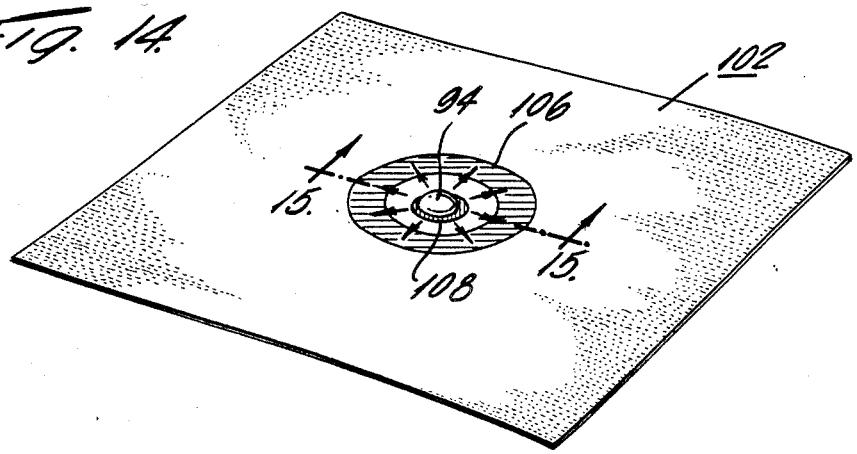
FIG. 14 is a perspective view similar to FIG. 12 wherein the carrier further contains a reagent and is indicative of a positive test, i.e., color formation in separated fluid portion.
Figure 15:
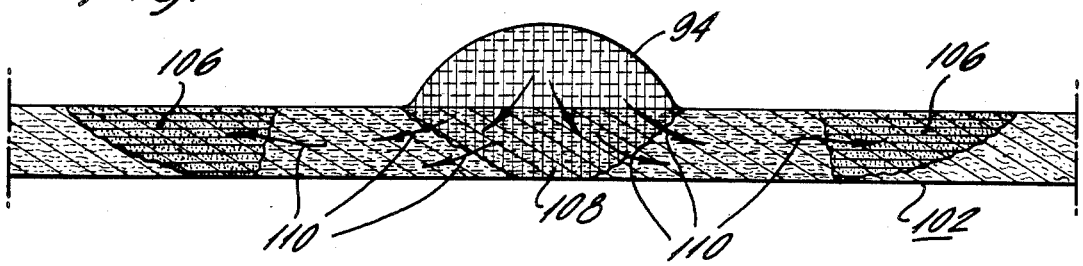
FIG. 15 is a greatly enlarged fragmentary sectional elevational view taken on the line 15—15 of FIG. 14.
Figure 16:
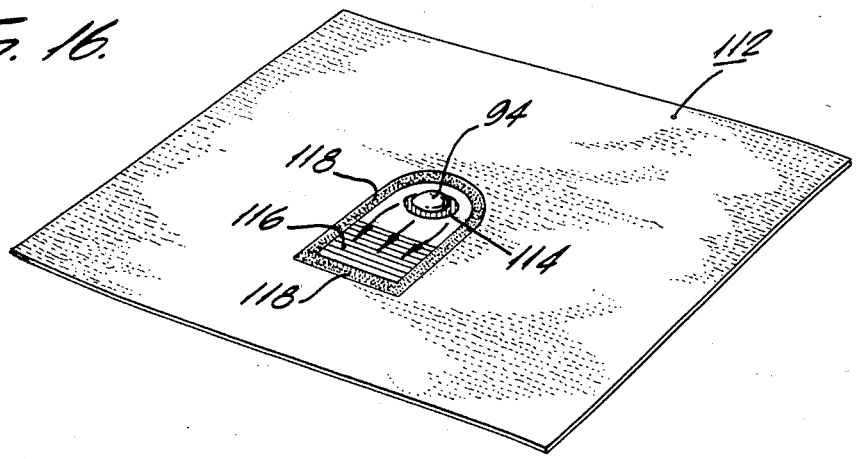
FIG. 16 is a further modification of FIG. 12 showing the separation of fluid from cellular material confined in an area by barrier means.

FIGS. 12 through 15 illustrate the invention in its simplest embodiment wherein the test device 90 consists of an absorbent material such as filter paper or the like containing a carbohydrate. A drop of whole blood 94 to be tested is applied to the absorbent material by pipette 92. The arrows 98 demonstrate the outward migration of the fluid 96 from the whole blood leaving the zone of cellular material 100 at the droplet site. FIG. 14 represents an absorbent carrier material 102 similar to FIG. 12 wherein the absorbent carrier further contains a reagent which gives a color reaction in the fluid zone area 106 if the component tested for is present. The cellular zone 108 remains at the droplet site 94. FIG. 16 depicts test device 116 comprising an absorbent carrier containing a carbohydrate and a reagent. A barrier 118 confines the migration of the blood fluid 116 within a limited area. The barrier may be any material which will prevent migration, for example, glue, a shellac, wax, or a synthetic resin such as an epoxy, phenolic, polyester or silicone resin commonly used in paper-resin laminates.

Figure 18:
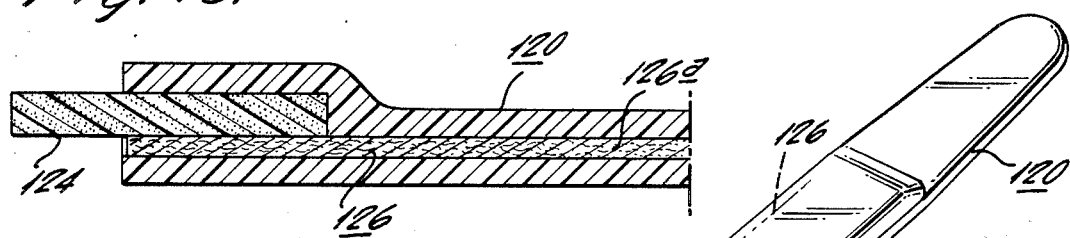
FIG. 18 is a greatly enlarged fragmentary sectional view taken on the line 18—18 of FIG. 17.
Figure 17:
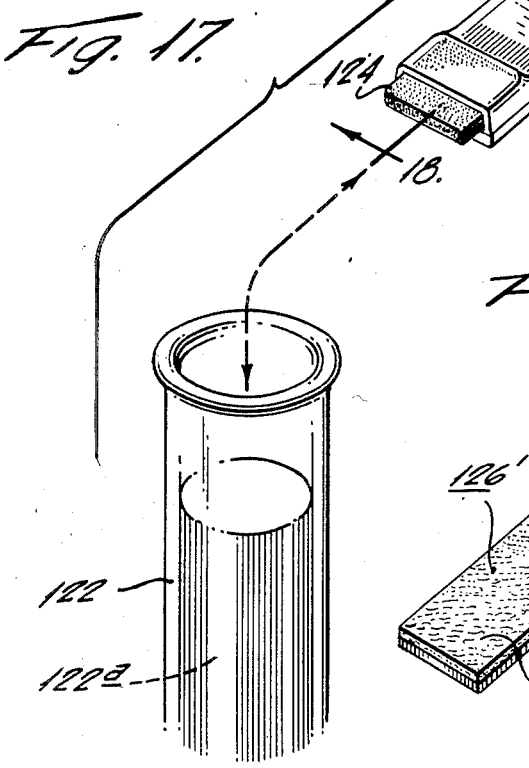
FIG. 17 is an exploded perspective view of still an additional modification in which the carrier containing the carbohydrate is attached to a rigid support and encased in said support.
Figure 19:
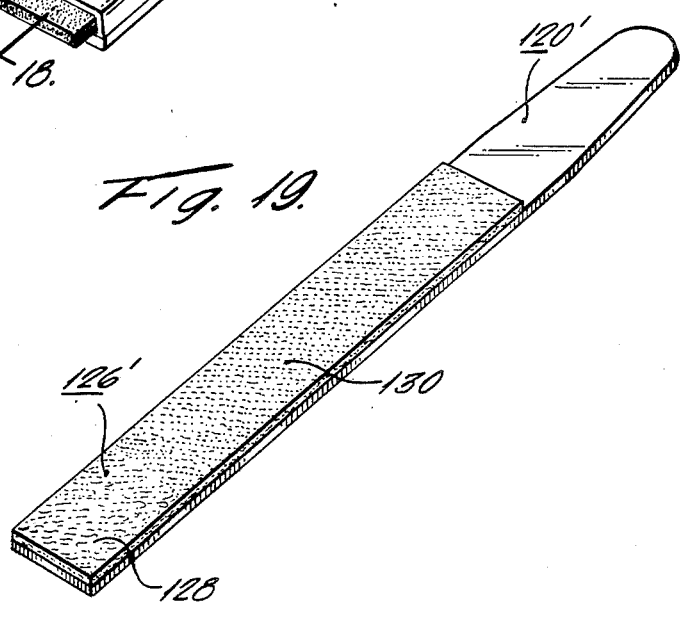
FIG. 19 is a further modification of FIG. 17 in which the carrier is not encased in the support.

A further modification of the device of this invention is illustrated as noted at FIGS. 17 through 19, where the absorbent material 124 and 126 is secured to rigid rectangular supports 120 and 120'.

Referring to FIG. 17 the absorbent material 126 is encased with a plastic covering and a portion of the material 124 extends beyond the enclosure. The support has been removed from a test tube 122 containing the whole blood to be tested 122a and demonstrates a positive test at the color reactive zone 126a. FIG. 19 illustrates a modification of FIG. 17 showing the absorbent material 126 with the cellular zone 128 and color reactive zone (fluid zone) 130 not encased but completely exposed.

The above embodiments are illustrative and are not intended to be limiting.

The following examples also serve to merely illustrate and not limit a method of preparing the testing device.

EXAMPLE 1

An alcoholic suspension of mannitol was prepared. The suspension was continually stirred while depositing the suspended powder onto approximately a 0.002 inch thick mylar carrier with an adhesive precoat. The band of mannitol was deposited to the following dimensions, 0.25 inches wide and 0.004 inches thick. The suspended mannitol powder was thoroughly dried and overlaid with a plastic carrier.

EXAMPLE 2

A band of mannitol was prepared as in Example 1. A polycarbonate carrier coated with glucose oxidase, peroxidase, buffer and a chromogen combination was laminated to the mylar carrier.

The resulting sandwich like structure was cut into appropriate size strips to be employed as testing devices.

EXAMPLE 3

100 ml. of an aqueous solution of 20% mannitol was prepared. A 2×2 inch piece of Whatman #1 filter paper was saturated with the above solution and dried in an oven at 50° C.

EXAMPLE 4

The filter paper as prepared in Example 3 was cut into two 1×2 inch strips and spotted with solutions of tetramethylbenzidine, glucose oxidase, peroxidase and buffer and dried.

What is claimed is:

1. A test device for separating the fluid portion from whole blood and detecting soluble components in whole blood which comprises a first impermeable carrier having applied thereon a sugar and a second impermeable carrier having incorporated thereon a test reagent specifically reactable with a component to be detected, said first and second carriers being affixed to one another substantially along their entire juxtaposed peripheral edges defining an opening there-between and so layered that the sugar and reagent are in contiguous facing relationship, wherein said opening and carriers permit capillary and longitudinal transport of the blood.

2. The device of claim 1 wherein the first carrier is a polyester and the second carrier is a polycarbonate.

3. The device of claim 1 wherein the first carrier is opaque and the second carrier is transparent.

4. The device of claim 1 wherein the sugar is mannitol.

5. A method for separating whole blood into fluid and cellular fractions which comprises applying the blood to the device of claim 1 whereby the cellular fraction remains in close proximity to the site of contact and the fluid fraction migrates in a longitudinal fashion away from said site.

6. The method of claim 5 wherein the sugar is mannitol.

* * * * *